(12) United States Patent
Swift et al.

(10) Patent No.: US 12,406,770 B2
(45) Date of Patent: Sep. 2, 2025

(54) HYBRID PREDICTIVE MODEL FOR ALERTNESS MONITORING

(71) Applicant: International Business Machines Corporation, Armonk, NY (US)

(72) Inventors: Mary D. Swift, Rochester, NY (US); Donna K. Byron, Petersham, MA (US); Ashok Kumar, North Chelmsford, MA (US)

(73) Assignee: International Business Machines Corporation, Armonk, NY (US)

( * ) Notice: Subject to any disclaimer, the term of this patent is extended or adjusted under 35 U.S.C. 154(b) by 1607 days.

(21) Appl. No.: 16/238,877

(22) Filed: Jan. 3, 2019

(65) Prior Publication Data
US 2020/0219616 A1 Jul. 9, 2020

(51) Int. Cl.
*G06N 20/00* (2019.01)
*G06N 5/043* (2023.01)
*G06N 7/01* (2023.01)
*G16H 10/60* (2018.01)
*G16H 50/20* (2018.01)

(52) U.S. Cl.
CPC .............. *G16H 50/20* (2018.01); *G06N 5/043* (2013.01); *G06N 7/01* (2023.01); *G06N 20/00* (2019.01); *G16H 10/60* (2018.01)

(58) Field of Classification Search
CPC ........ G16H 50/20; G16H 10/60; G16H 50/30; G06N 20/00; G06N 5/043; G06N 7/005; G06F 16/35; G06F 21/6245; G06Q 10/10; G06Q 10/06
See application file for complete search history.

(56) References Cited

U.S. PATENT DOCUMENTS

| 6,773,396 B2 | 8/2004 | Flach et al. |
| 10,319,476 B1 * | 6/2019 | LaBorde .................. G06N 3/08 |

(Continued)

OTHER PUBLICATIONS

Mell et al., "The NIST Definition of Cloud Computing", National Institute of Standards and Technology, U.S. Dept. of Commerce, NIST Special Publ. 800-145, Sep. 2011, 7 pages.

(Continued)

*Primary Examiner* — Casey R. Garner
(74) *Attorney, Agent, or Firm* — Gavin Giraud, Esq.; Rachel L. Pearlman, Esq.; Heslin Rothenberg Farley & Mesiti P.C.

(57) ABSTRACT

A method, computer program product, and a system where a processor(s) obtains data related to medical treatment and a current physical state of a given patient. The processor(s) cognitively analyzes the data to identify potential patient behavioral patterns of the given patient. The processor(s) obtains general patient data and correlates the general patient data with a portion of the data to identify elements in the general patient data with a potential impact on the identified potential patient behavioral patterns. The processor(s) determines impacts of the elements on the identified potential behavioral patterns and applies the impacts to generate a data structure comprising baseline behavioral patterns, i.e., a predictive model to utilize in determining probabilities that the given patient will exhibit behaviors comprising the baseline behavioral patterns during a defined future time interval.

20 Claims, 6 Drawing Sheets

(56) References Cited

U.S. PATENT DOCUMENTS

| | | | | |
|---|---|---|---|---|
| 2002/0183644 | A1* | 12/2002 | Levendowski | A61B 5/7207 |
| | | | | 600/544 |
| 2003/0144829 | A1* | 7/2003 | Geatz | G16H 10/60 |
| | | | | 703/22 |
| 2014/0095181 | A1 | 4/2014 | Johnson et al. | |
| 2014/0136233 | A1* | 5/2014 | Atkinson | G16H 15/00 |
| | | | | 705/3 |
| 2016/0147946 | A1* | 5/2016 | Von Reden | G16H 10/60 |
| | | | | 705/3 |
| 2017/0231561 | A1* | 8/2017 | Sutoko | G16H 10/20 |
| | | | | 702/19 |
| 2017/0238868 | A1 | 8/2017 | Kenyon et al. | |
| 2018/0005645 | A1* | 1/2018 | Khaleghi | G16H 50/20 |
| 2018/0116560 | A1 | 5/2018 | Quinn et al. | |
| 2018/0174675 | A1* | 6/2018 | Roy | A61M 5/14244 |
| 2020/0098456 | A1* | 3/2020 | Loscutoff | G06F 9/542 |
| 2020/0152332 | A1* | 5/2020 | Yang | G16H 50/20 |

OTHER PUBLICATIONS

"Remote Patient Monitoring—Center for Connected Health Policy", The National Telehealth Policy Resource Center, Mar. 18, 2025, 05 pages.

"The Ultimate Guide to Sleep Tracking", Sleep Junkies, Feb. 28, 2018, 16 pages.

Family Visitation in the Adult Intensive Care Unit, AACN Practice Alert, Feb. 1, 2016, vol. 36, No. 1, pp. e15-e19.

Mimic 2 Databases, https://physionet.org/mimic2/, Mar. 18, 2025, 03 pages.

* cited by examiner

HYBRID PREDICTIVE MODEL FOR ALERTNESS MONITORING

BACKGROUND

When patients are hospitalized, one of the bright spots for many patients is having friends and family members visit. Visits from friends and family are important to patients because of the companionship that friends and family provide can be psychological benefits to the patients, but also, patients, who are regularly visited by friends and family, can receive heightened attention from hospital staff. Many patients can also rely on certain of their visitors to act as healthcare advocates on their behalf. Because of the nature of a hospital stay, it may be difficult for these invited and desired visitors to time their visits in a manner that is most desired and advantageous to the patient. Even if friends and family, at the request of the patient, seek to be nearby to support the patient, much of the time, it may be difficult to time their visits to provide the most benefits to the patients. During a hospital stay, the patient may be unconscious, sleeping, or sedated, so there may only be short periods when the patient is awake and alert and would welcome or benefit from visitors. Many patients hope that their friends and family (or selected members of their friends and family) are able to find these short windows for visits, so that they can spend quality time with the patient such that the patient realizes benefits from the visits. Unfortunately, a patient may not know his or her schedule in advance and visiting hours alone are not a definitive guide to when a given patient would like to be visited. These alertness windows can be unpredictable and occur at any time of the day or night. When friends and family members are forced to guess as to when these windows may occur, they may arise at inconvenient times and the patient will not benefit from their visits. Knowing when a patient, who has previously indicated that he or she is interested in receiving visitors, is in a condition to receive visitors (e.g., awake and alert) is valuable information for friends and family members because this information allows patients to make the most of the time that they can interact with their visitors and secondarily, allows the visitors to have a more productive visit, because the patient is in a wakeful state.

SUMMARY

Shortcomings of the prior art are overcome and additional advantages are provided through the provision of a method for predicting patient behavior in future time periods. The method includes, for instance: progressively obtaining, by one or more processors, data related to medical treatment and a current physical state of a given patient from a patient monitoring system, an electronic medical records system, and a scheduling system; cognitively analyzing, by the one or more processors, the data to identify potential patient behavioral patterns of the given patient; obtaining, by the one or more processors, general patient data; correlating, by the or more processors, the general patient data with a portion of the progressively obtained data to identify one or more elements in the general patient data with a potential impact on the identified potential patient behavioral patterns; determining, by the one or more processors, impacts of the one or more elements on the identified potential behavioral patterns and applying the impacts to generate a data structure comprising baseline behavioral patterns, wherein the data structure comprises a predictive model to utilize in determining one or more probabilities that the given patient will exhibit one or more behaviors comprising the baseline behavioral patterns during a defined future time interval; applying, by the one or more processors, the predictive model, to the defined future time interval, wherein the applying comprises generating a timeline comprising the future time interval, wherein the timeline is segmented into one or more sub-intervals, wherein a probability of the one or more probabilities is assigned to each sub-interval of the one or more sub-intervals; and transmitting, by the one or more processors, the timeline to authorized users, via computing nodes communicatively coupled to the one or more processors via an Internet connection.

Shortcomings of the prior art are overcome and additional advantages are provided through the provision of a computer program product for predicting patient behavior in future time periods. The computer program product comprises a storage medium readable by a processing circuit and storing instructions for execution by the processing circuit for performing a method. The method includes, for instance: progressively obtaining, by the one or more processors, data related to medical treatment and a current physical state of a given patient from a patient monitoring system, an electronic medical records system, and a scheduling system; cognitively analyzing, by the one or more processors, the data to identify potential patient behavioral patterns of the given patient; obtaining, by the one or more processors, general patient data; correlating, by the or more processors, the general patient data with a portion of the progressively obtained data to identify one or more elements in the general patient data with a potential impact on the identified potential patient behavioral patterns; determining, by the one or more processors, impacts of the one or more elements on the identified potential behavioral patterns and applying the impacts to generate a data structure comprising baseline behavioral patterns, wherein the data structure comprises a predictive model to utilize in determining one or more probabilities that the given patient will exhibit one or more behaviors comprising the baseline behavioral patterns during a defined future time interval; applying, by the one or more processors, the predictive model, to the defined future time interval, wherein the applying comprises generating a timeline comprising the future time interval, wherein the timeline is segmented into one or more sub-intervals, wherein a probability of the one or more probabilities is assigned to each sub-interval of the one or more sub-intervals; and transmitting, by the one or more processors, the timeline to authorized users, via computing nodes communicatively coupled to the one or more processors via an Internet connection.

Methods and systems relating to one or more aspects are also described and claimed herein. Further, services relating to one or more aspects are also described and may be claimed herein.

Additional features are realized through the techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

Figure 1:
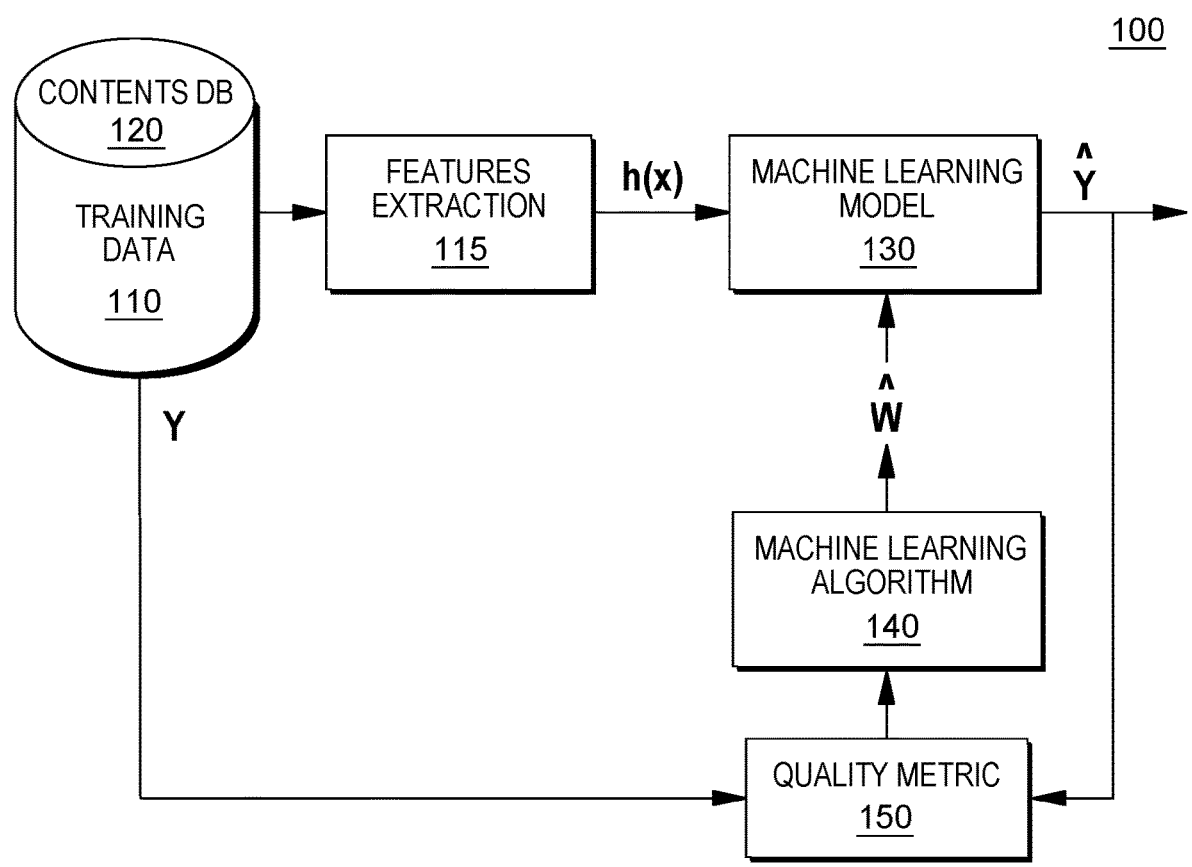
FIG. 1 is a workflow illustrating certain aspects of an embodiment of the present invention.

The accompanying figures, in which like reference numerals refer to identical or functionally similar elements throughout the separate views and which are incorporated in and form a part of the specification, further illustrate the present invention and, together with the detailed description of the invention, serve to explain the principles of the present invention. As understood by one of skill in the art, the accompanying figures are provided for ease of understanding and illustrate aspects of certain embodiments of the present invention. The invention is not limited to the embodiments depicted in the figures.

Figure 4:
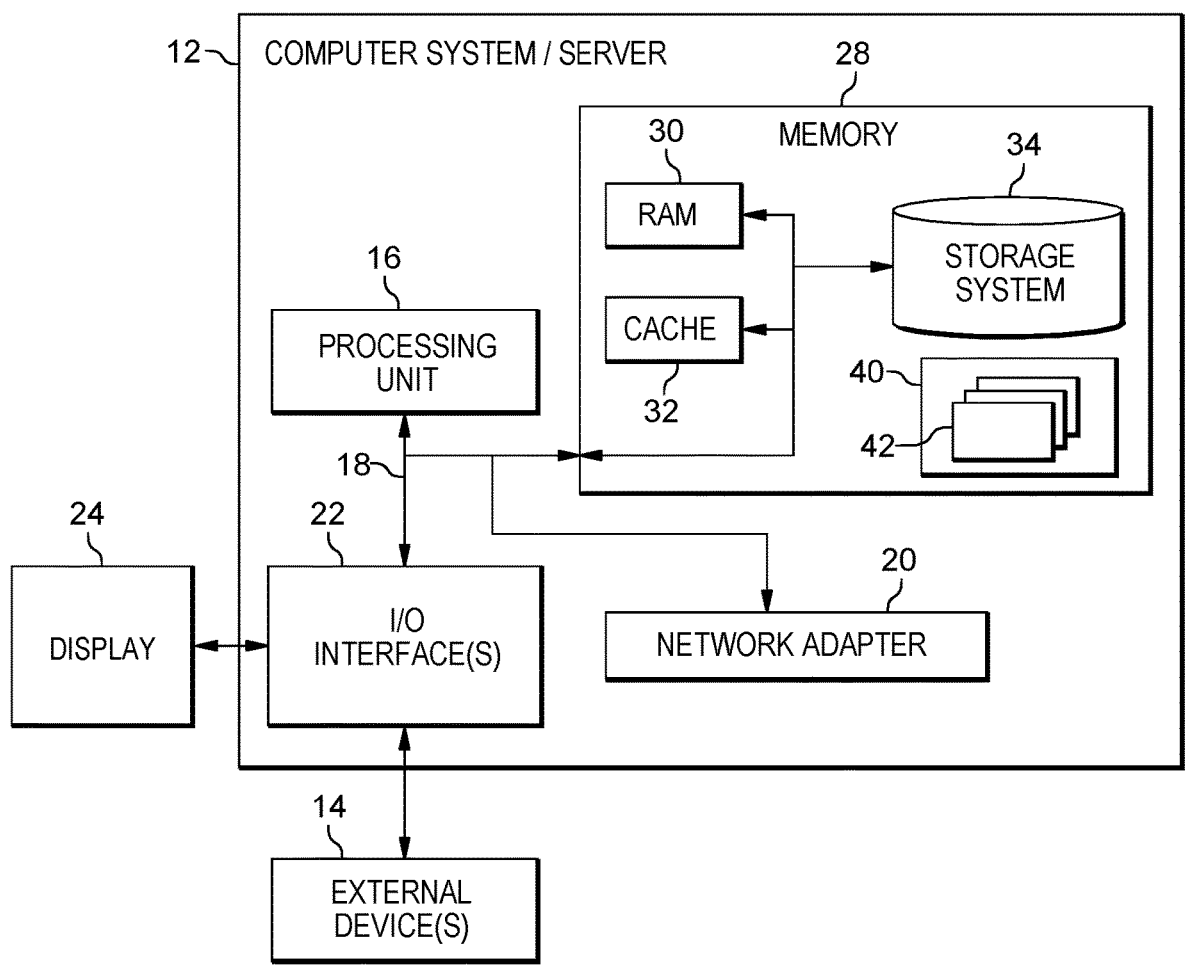
FIG. 4 depicts one embodiment of a computing node that can be utilized in a cloud computing environment.

As understood by one of skill in the art, program code, as referred to throughout this application, includes both software and hardware. For example, program code in certain embodiments of the present invention includes fixed function hardware, while other embodiments utilized a software-based implementation of the functionality described. Certain embodiments combine both types of program code. One example of program code, also referred to as one or more programs, is depicted in FIG. 4 as program/utility 40, having a set (at least one) of program modules 42, may be stored in memory 28.

Embodiments of the present invention include a computer-implemented method, a computer program product, and a computing system where program code executing on one or more processors enables a patient to communicate a desire to be visited at certain times by select visitors. With the express permission of the patient and in keeping with privacy restrictions related to personal information, program code in some embodiments of the present invention aggregates patient data from multiple diverse sources, including, but not limited to, sensor data, treatment information and event scheduling, and generates a model to predict wakefulness and alertness of the patient for particular time increments. In some embodiments of the present invention, the program code transmits (or otherwise makes available) the generated wakefulness information to subscribed parties, approved by the patient, such that the parties receive customized alerts. Utilizing the customized alerts, the parties are provided, by the program code, with an overview of windows of opportunity for interaction with the patient, as the patient has previously consented to, and is able to, interact with these parties when he or she is alert and awake. Program code in embodiments of the present invention predicts wakefulness patterns, the utilization of which to enable meaningful visiting of the patient to whom the data inputs, which the program code utilizes to generate the patterns or model, are relevant.

Embodiments of the present invention are inextricably tied to computing and provide significantly more than existing technological approaches which are primarily concerned merely with patient monitoring. First, embodiments of the present invention enable program code executing on one or more processors to exploit the interconnectivity of various systems as well as utilize various computing-centric data analysis and handling techniques in order to generate a continuously-updated predictive model. The program code applies the predictive model in order to provide customized temporal alerts to authorized users identified by the program code. Both the interconnectivity of the computing systems utilized as well as the computer-exclusive data processing techniques utilized by the program code enable various aspects of the present invention. Second, embodiments of the present invention provide significantly more when monitoring patients because both the data utilized in embodiments of the present invention and the actions taken by the program code responsive to analyzing the data provide advantages over existing patient monitoring systems. Generally, rather than merely monitoring a patient, in embodiments of the present invention, program code executing of at least one processing resource, provides a patient with the ability to personally manage visitors in a manner that benefits the patient by informing desired visitors of times when visits to the patients would be productive (e.g., allow the patient to enjoy the company of the visitors and allow the patients to invite visitors who can advocate on the patient's behalf). For example, although some existing systems utilize patient sensor data to infer sleep stages of a patient in order to evaluate the patient's sleep needs, in order to perform a cost/benefit analysis when deciding whether to schedule certain therapies, these systems cannot generate models that predict the alertness of the patient in a given upcoming time period. Unlike embodiments of the present invention, these existing systems do not utilize (with pre-authorization) data related to medications the patient is taking, which enable program code in embodiments of the present invention to generate accurate future wakefulness predictions and transmit alerts, based in part on the program code integrating potential effects of medications on sleep patterns into the model generated by the program code. Similarly, certain existing patient monitoring systems use patient sensor data from a wearable device, a patient's medical history, and user input, to model an individual's circadian rhythm and sleep-wake cycle alertness and fatigue scores and display the scores on charts. Not only do these existing systems rely solely on the use of wearable devices, which can be utilized in embodiments of the present invention but are not essential to proper operation, but these existing systems also do not utilize patient medication data in their predictive modeling. Additionally, unlike the program code in embodiments of the present invention, these existing systems cannot trigger alerts authorized by a patient, automatically, based on determining that a patient is awake at a time that is not consistent with the model generated by the program code and cannot update the model to account for this anomaly, moving forward. In addition, these existing systems do not integrate a schedule of a patient (e.g., according to a calendar system) into a wakefulness model. The integration of this information enables program code in embodiments of the present invention to determine not only when a patient is awake (or otherwise in a state where visitors would be ideal) but also provide availability windows to authorized (or invited) visitors at times when the patient is not otherwise engaged in pre-scheduled activities, including but not limited to, medical procedures and tests. Thus, the prediction model generated by the program code in embodiments of the present invention is more comprehensive (and accurate) than existing patient monitoring systems in part because: 1) the program code in embodiments of the present invention obtains and analyzes scheduled events as well as medications a patient is taking when generating an alertness prediction model; and 2) the program code can generate ad-hoc alerts to subscribers when a patient wakes, notifying these users of an opportunity that might otherwise be missed (e.g., if it occurs outside a predicted window per the generated model).

Embodiments of the present invention provide various advantages over existing patient monitoring systems from a usability standpoint in that it provides direct benefits to the patient. Current practice focuses on the present state of the physical patient, but does not provide predictive information, as authorized by the patient, for the caregivers, including friends and family members, who the patient would like to have visit. Because this type of information is not available, friends and family generally must be physically present in the room with a patient, or must contact the patient's care unit in order to determine whether the timing is right for visiting the patient, based on whether the patient is alert. Privacy measures, such as patient codes and logistics and otherwise engaged caregivers, can hinder the ability of a prospective visitor in receiving accurate alertness information about a patient. Additionally, there are no mechanisms, outside of making a phone call with a hospital phone, in which a patient can invite specific family and/or friends to visit at a time when the patient is available. Once the patient makes the call, the patient may no longer be available for the visit, thus, the time window was used for the call, instead of for a visit, and is missed.

In contrast to these problematic approaches, in embodiments of the present invention, based on a patient's desire to receive visitors when awake, program code executing on at least one processor provides prospective visitors and caregivers with a customized forecast of likely times of wakefulness and availability for a patient. Approved subscribers (who have been approved by the patient and in some cases, a proxy designed by the patient) can securely receive this availability information, eliminating the need for phone calls or in-person visits to determine wakefulness of a patient.

Embodiments of the present invention provide advantages to patients, themselves, which are not realized in existing patient monitoring approaches. In some embodiments of the present invention, a patient can elect or decline to provide the patient's wakefulness information to various subscribers. For example, in some embodiments of the present invention, the patient can vet subscribers, through an administrative interface, and decide who of the subscribers should receive alerts. A patient can also designate a proxy to make these decisions. The patient may also subscribe individuals or assign subscribers to different tiers, enabling or disabling the subscribers from receiving alerts. In order to protect the privacy of the patient, although some embodiments of the present invention, with the permission of the patient, access personal device information, health information, etc., when providing alerts to individuals approved by the patient to receive the alerts, in embodiments of the present invention, the program code does not include personal data in the alerts. For example, in some embodiments of the present invention, the program code may send a generic message that identifies the patient by an alias only know to approved subscribers and indicates present or future times to visit the patient, but does not indicate the location of the patient, as this would be previously known to the approved visitor.

As explained herein, the program code consistently and dynamically updates the model (wakefulness patterns), thus regularly increasing the accuracy of the predictions provided to the pre-approved subscribers, optionally based on the preferences of the patients related to those subscribers. FIG. 1, which will be discussed herein, illustrates a machine learning process utilized by program code in embodiments of the present invention to formulate wakefulness patterns for a given patient. In addition to providing a benefit to patients themselves, embodiments of the present invention also provide a benefit to hospital staff (or other treatment facility staff) who were earlier engaged in providing wakefulness information to callers, by eliminating this activity from their purview. Because the wakefulness information provided by the program code is relevant to time periods in the future, as well as more current time periods, the approved subscribers can plan their visits with a given patient, if they are anticipating missing a given window. This advance notice provide a benefit to patients by encouraging a consistent flow of desires visitors to a patient.

Figure 2:
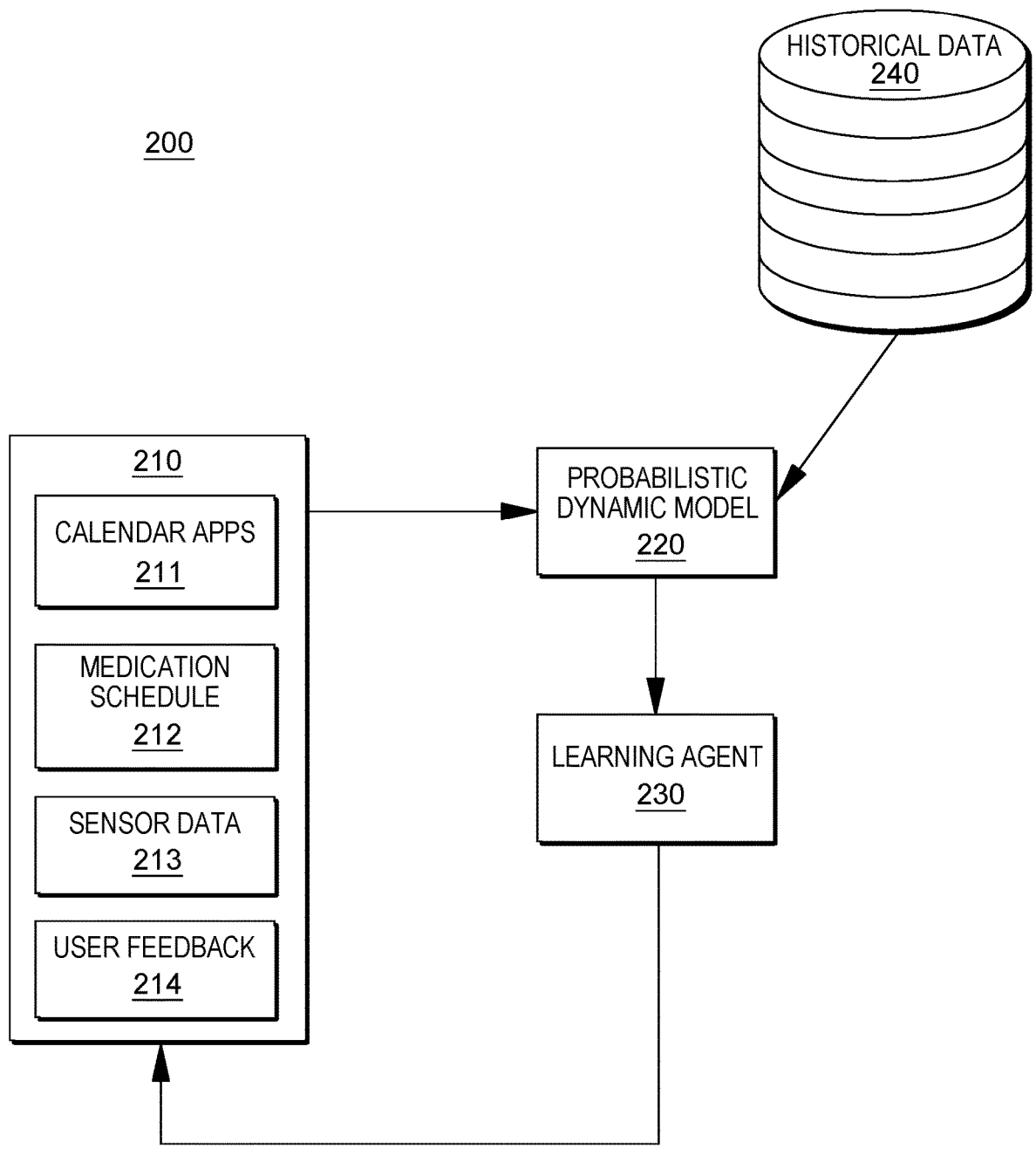
FIG. 2 is an illustration of a technical environment into which various aspects of an embodiment of the present invention can be implemented.

FIG. 2 illustrates elements of the technical environment 200 into which aspects of some embodiments of the present invention can be implemented. The program code in embodiments of the present invention, including the embodiment pictured in FIG. 1, generates a predictive model 220 and utilizes the predictive model 220 to inform, with a patient's permission, various users (e.g., subscribers) of a predicted state of the patient at a time in the future, such that the various users have a greater probability of visiting the patient when the patient is awake and alert. In generating a predictive model 220, program code in embodiments of the present invention can utilize cognitive agents, machine learning algorithms, and can process elements of the model utilizing a neural network. FIG. 2 depicts the program code generating and utilizing a probabilistic dynamic model 220 (i.e., the predictive model) to predict wakefulness of one or more patients. As discussed in reference to FIG. 1, the program code can train a model 220 utilizing training data. This stage can also be understood as initializing the model 220. In FIG. 2, the program code initializes the model 220 by utilizing conditional probability tables. The program code builds the tables by obtaining historical data 240 to establish key dependencies between physiological data, sleep state, and the impact of specific medications on alertness. One such historical data 240 source that can be utilized by program code is the MIMIC III database, which is an openly available dataset developed by the Massachusetts Institute of Technology (MIT) Lab for Computational Physiology and includes de-identified health data associated with approximately 40,000 critical care patients. The data include, but are not limited to, demographics, vital signs, laboratory tests, and medications. One example of historical data 240 that the program code can utilize to initialize model 220 are physiological factors and medication-related factors that indicate a high probability that a patient is asleep: snoring, lower, heart rate, blood pressure, respiratory rate, and/or the ingestion of a sleeping pill within a specific time frame. The program code can utilize these factors to train the model 220 to predict that a given patient is not awake based on obtaining data related to the patient indicating the presence of one or more of these factors. This type of data is publicly available and does not include any personally identifiable information.

In some embodiments of the present invention, with the previous permission of the patient and any relevant administrative authorities, the program code obtains patient-specific data from a variety of different data sources 210, which the program code utilizes to update aspects of the initialized model 220 to customize the model 220 to the specific patient. In the pictured embodiment, data sources of relevant patient data utilized by the program code include: 1) sensor data 213; 2) medication scheduling data 212; 3) calendar events 211; and/or 4) user feedback 214.

Just as perspective visitors can subscribe in embodiments of the present invention and are approved by the patient before receiving alerts, the patient can also subscribe to participate, such that notifications can only be received about a patient with the permission of the patient. As part of the subscription process, the patient designates system from which the patient authorizes the program code to obtain data, including sensor data 213.

With the prior permission of the patient, the sensor data 213 can include data collected from one or more of continuous monitoring systems, which can include Internet of Things (IoT) devices and other environmental or personal computing devices with sensors. As understood by one of skill in the art, the Internet of Things (IoT) is a system of interrelated computing devices, mechanical and digital machines, objects, animals and/or people that are provided with unique identifiers and the ability to transfer data over a network, without requiring human-to-human or human-to-computer interaction. These communications are enabled by smart sensors, which include, but are not limited to, both active and passive radio-frequency identification (RFID) tags, which utilize electromagnetic fields to identify automatically and to track tags attached to objects and/or associated with objects and people. Smart sensors, such as RFID tags, can track environmental factors related to an object, including but not limited to, temperature and humidity. The smart sensors can be utilized to measure temperature, humidity, vibrations, motion, light, pressure and/or altitude. IoT devices also include individual activity and fitness trackers, which include (wearable) devices or applications that include smart sensors for monitoring and tracking fitness-related metrics such as distance walked or run, calorie consumption, and in some cases heartbeat and quality of sleep and include smartwatches that are synced to a computer or smartphone for long-term data tracking. IoT devices also include Smart home devices, digital assistants, and home entertainment devices. Because the smart sensors in IoT devices carry unique identifiers, a computing system that communicates with a given sensor can identify the source of the information. Within the IoT, various devices can communicate with each other and can access data from sources available over various communication networks, including the Internet. Thus, the program code in some embodiments of the present invention utilizes data obtained from various IoT devices to generate or update the model 220 utilized by the program code to predict alertness and wakefulness of a given individual (patient), within specific time intervals.

In some embodiments of the present invention, the sensor data 213 is physiological data from the aforementioned continuous bed-side monitoring and includes, but is not limited to, cardiovascular measures (e.g., heart rate, blood pressure, blood oxygen saturation, and respiration), body positioning and movement data (e.g., rest versus activity data), body temperature, and environmental conditions of the environment of the patient (e.g., ambient light and/or noise). The program code updates the model 220 in real-time, upon receipt of the sensor data 213, including sensor data that deviates from the model 220, program code of the learning agent 230 utilizes this sensor data 213 to continually learn and updates the patterns that form the model 220. An event that would trigger the program code to update the model 220 in real-time would be the sensor data 230 indicating that the patient is awake, for example if the patient wakes in the middle of the night when the patient is predicted, based on the model 220, to be sleeping.

With the prior permission of the patient and relevant record administrators, the program code obtains medication scheduling information 212 from sources including, but not limited to, electronic medical records, and/or a treatment scheduling system. Based on the initialization data, the program code can utilize this medication scheduling information 212 to predict when, at a future time proximate to receiving specified medication, the alertness or wakefulness of the patient can be impacted by the medication, by applying the model 220 to the scheduling of the medication 212. In some embodiments of the present invention, the program code obtains exclusively medication and scheduling information, but cannot access any additional information in the patient's electronic medical records. Provided the access is authorized, during the initialization of the model 220, the program code obtains historical data 240 that the program code can utilize to improve pattern detection and prediction (generating and updating the model 220) for the given patient. For example, the program code of the learning agent 230 can incorporate data from existing patient databases for similar use case history to determine the likely effects of the medications on the patient and the impact of the medication of the wakefulness patterns of the patient. The program code can adjust the model in accordance with these learned patterns.

In some embodiments of the present invention, the patient and relevant record administrators authorize access to the patient's calendar so that the program code can obtain calendar events 211. If authorized, the calendar events 211 obtained by the program code include scheduled tests and procedures, which the program code can obtain from a calendaring application. The program code utilizes the scheduled events to adjust periods it predicts as wakeful or alert for the patient. Although the program code can utilize the model 220 and determine that the patient is likely awake during a period in the future in which a test or procedure is scheduled, the program code will not recommend this future period for a visit with the patient because the patient will be engaged with the tests and/or procedures and therefore unable to receive visitors. Scheduled events or calendar events 211 may include, but are not limited to, tests, physical therapy or periodic vital signs checks. Program code incorporates calendar events 211 into the model so because a scheduled calendar event 211 also indicates that a patient will be awake at a specific time and in a predicted location.

The program code applies machine learning algorithms to generate and train algorithms to generate a model utilized to predict wakefulness and/or alertness, of a given individual. In the aforementioned initialization stage, the program code trains these algorithms, based on patterns for a given patient (and/or across all patients with certain shared attributes). FIG. 1 is an example of a machine learning training system 100 that can be utilized to perform cognitive analyses of various inputs, including the general initialization data, the historical data 240. However, training data utilized to train the model in embodiments of the present invention can also include historical data that is personalized to the patient, including but not limited to: 1) sensor data (e.g., physiological data from patient monitoring including cardiovascular measures such as heart rate, blood pressure, blood oxygen saturation, respiration, rest versus activity data from body movement and body position, temperature, and ambient light and noise readings); 2) medication scheduling information; 3) calendar events (e.g., scheduled tests and procedures); and/or 4) user feedback provided responsive to queries on the accuracy of various predictions (e.g., communicated through an application interface). In some embodiments of the present invention, personalized patient data includes patient condition (e.g., reason for hospitalization/treatment). The program code in embodiments of the present invention performs a cognitive analysis to generate data structures, including algorithms utilized by the program code to predict states of a given patient. Machine learning (ML) solves problems that cannot be solved with numerical means alone. In this ML-based example, program code extracts various features/attributes from training data 140 (e.g., historical data collected from various data sources relevant to the patient and general data), which may be resident in one or more databases 120 comprising patient-related data and general data. The features are utilized to develop a predictor function, h(x), also referred to as a hypothesis, which the program code utilizes as a machine learning model 130. In identifying various patient states and/or behaviors indicative of states in the training data 110, the program code can utilize various techniques including, but not limited to, mutual information, which is an example of a method that can be utilized to identify features in an embodiment of the present invention. Further embodiments of the present invention utilize varying techniques to select features (elements, patterns, attributes, etc.), including but not limited to, diffusion mapping, principal component analysis, recursive feature elimination (a brute force approach to selecting features), and/or a Random Forest, to select the attributes related to various patient states. The program code may utilize a machine learning algorithm 140 to train the machine learning model 130 (e.g., the algorithms utilized by the program code), including providing weights for the conclusions, so that the program code can train the predictor functions that comprise the machine learning model 130. The conclusions may be evaluated by a quality metric 150. By selecting a diverse set of training data 110, the program code trains the machine learning model 130 to identify and weight various attributes (e.g., features, patterns) that correlate to various states of a patient.

Returning to FIG. 2, the model 220 generated by the program code is self-learning as the program code updates the model 220 based on active user feedback 214 received from users (e.g., subscribers) as well as from the passive feedback received from the sensor data 213, related to monitoring the patient. For example, when the program code determines that a patient is alert at a given time that was not previously predicted by the model 220, the program code alerts the users, but also, utilizes a learning agent 230 to update the model 220 to reflect the state of the patient, in order to improve predictions in the future. Additionally, when the program code alerts the users that a patient is anticipated to be alert during a given period of time and the program code determines that this prediction was incorrect, either based on receiving user feedback through an interface or based on continuously monitoring the patient, the program code updates the model 220 to reflect the inaccuracy of the prediction for the given period of time. Program code comprising a learning agent 230 cognitively analyzes the data deviating from the modeled expectations and adjusts the model 220 in order to increase the accuracy of the model, moving forward.

In some embodiments of the present invention, program code executing on one or more processors, utilizes an existing cognitive analysis tools or agents to tune the model 220, based on data obtained from the various data sources 210, including the sensor data 213. Some embodiments of the present invention utilize IBM Watson® as the cognitive agent. IBM Watson® is a product of International Business Machines Corporation. IBM Watson® is a registered trademark of International Business Machines Corporation, Armonk, New York, US. In embodiments of the present invention, the program code interfaces with IBM Watson® APIs to perform a cognitive analysis of obtained data, in some embodiments of the present invention, the program code interfaces with the application programming interfaces (APIs) that are part of a known cognitive agent, such as the IBM Watson® Application Program Interface (API), a product of International Business Machines Corporation, to determine impacts of sensor data 213 and other data on wakefulness patterns and to update the model 220, accordingly.

In some embodiments of the present invention, the program code trains aspects of the IBM Watson® Application Program Interface (API) to learn the relationships between physiological elements from the sensors 213 and the wakefulness patterns of the patient. Utilizing an existing cognitive agent, such as IBM Watson® expands the type of patient data that the program code can integrate into the model 220. For example, sensors data 213 can include documentary, visual, and audio data, which the program code can process, based on its utilization of IBM Watson®. Specifically, in some embodiments of the present invention, certain of the APIs of the IBM Watson® API comprise a cognitive agent (e.g., learning agent 230) that includes one or more programs, including, but are not limited to, natural language classifiers, Retrieve and Rank (i.e., a service available through the IBM Watson® Developer Cloud that can surface the most relevant information from a collection of documents), concepts/visual insights, trade off analytics, document conversion, and/or relationship extraction. In an embodiment of the present invention, one or more programs analyze the data obtained by the program code across various sources utilizing one or more of a natural language classifier, retrieve and rank APIs, and trade off analytics APIs. The IBM Watson® Application Program Interface (API) can also provide audio related API services, in the event that the collected data includes audio, which can be utilized by the program code, including but not limited to natural language processing, text to speech capabilities, and/or translation.

In generating and updating the model 220, the program code can segment future periods into distinct portions, in order to provide users with a useable guide for anticipating the state of a patient. In some embodiments of the present invention, the program code divides each twenty-four (24) hour period into defined time segments of a certain length (e.g., twenty (20) minutes). The program code can generate an average state prediction for each distinct period, for example, by synthesizing or averaging the data (e.g., sensor data 213) over each time segment. The program code can overlays both the calendar events 211 and scheduled medication 213 over these segments and utilize the model 220 to adjust sensor-based state predictions for these segments.

The program code can provide state predictions and/or alerts for a given patient as varying values. In some embodiments of the present invention, the program code calculates a binary wakefulness value for the patient, which the program code provides to users (e.g., subscribers). Thus, in some embodiments of the present invention, the program code indicates to a user whether a given patient is predicted to be awake or alert during a given future time period. In other embodiments of the present invention, the program code provides the user with an indicator of one or more of: 1) a probability that a patient is awake or alert during a given future period of time; and/or 2) a degree of anticipated wakefulness during the time period. As discussed above, in embodiments of the present invention, should the patient behavior deviate from the model 220 predictions, based on continuously monitoring the patient (e.g., utilizing IoT devices and other computing devices including environmental and/or personal sensors 213), the program code can immediately alert users, for example, when the patient is awake. Whether users receive these immediate alerts may depend upon a location of the user. For example, if the program code determines that a given user is within a geographic range where this user could reach the patient during the period of wakefulness, the program code alerts the user that the patient is awake. The program code can make this determination based on accessing location services on a computing device associated with the user, accessing environmental sensors in the patient care facility, and referencing the model 220 to determine how long periods of wakefulness of the patient are anticipated to last. Thus, the program code determines, based on these inputs, a probability of the user reaching the patient while the patient is awake. If the probability meets a given threshold, the program code notifies the user of the patient's state.

In some embodiments of the present invention, the program code utilizes a neural network to analyze patient-related data to generate the model 220 utilized to predict the state of a given patient at a given time. Neural networks are a biologically-inspired programming paradigm which enable a computer to learn from observational data, in this case, sensor data, medication scheduling information, calendar events, and/or user feedback. This learning is referred to as deep learning, which is a set of techniques for learning in neural networks. Neural networks, including modular neural networks, are capable of pattern (e.g., state) recognition with speed, accuracy, and efficiency, in situations where data sets are multiple and expansive, including across a distributed network, including but not limited to, cloud computing systems. Modern neural networks are non-linear statistical data modeling tools. They are usually used to model complex relationships between inputs and outputs or to identify patterns (e.g., states) in data (i.e., neural networks are non-linear statistical data modeling or decision making tools). In general, program code utilizing neural networks can model complex relationships between inputs and outputs and identify patterns in data. Because of the speed and efficiency of neural networks, especially when parsing multiple complex data sets, neural networks and deep learning provide solutions to many problems in multiple source processing, which the program code in embodiments of the present invention accomplishes when obtaining data and generating a model for predicting states of a given patient during particular intervals.

Some embodiments of the present invention may utilize a neural network (NN) to predict future states of a given patient. Utilizing the neural network, the program code can predict the likelihood of the patient being in a given state at a subsequent time. The program code obtains (or derives) data related to the patient from various sources to generate an array of values (possible states) to input into input neurons of the NN. Responsive to these inputs, the output neurons of the NN produce an array that includes the predicted states. The program code can automatically transmit notifications related to the predicted states based on the perceived validity.

In some embodiments of the present invention, a neuromorphic processor or trained neuromorphic chip can be incorporated into the computing resources executing the program code. One example of a trained neuromorphic chip that is utilized in an embodiment of the present invention is the IBM® TrueNorth chip, produced by International Business Machines Corporation. IBM® is a registered trademark of International Business Machines Corporation, Armonk, New York, U.S.A. Other names used herein may be registered trademarks, trademarks or product names of International Business Machines Corporation or other companies.

The IBM® TrueNorth chip, also referred to as TrueNorth, is a neuromorphic complementary metal-oxide-semiconductor (CMOS) chip. TrueNorth includes a manycore network on a chip design (e.g., 4096 cores), each one simulating programmable silicon "neurons" (e.g., 256 programs) for a total of just over a million neurons. In turn, each neuron has 256 programmable synapses that convey the signals between them. Hence, the total number of programmable synapses is just over 268 million ($2^{28}$). Memory, computation, and communication are handled in each of the 4096 neurosynaptic cores, so TrueNorth circumvents the von-Neumann-architecture bottlenecks and is very energy-efficient.

Figure 3:
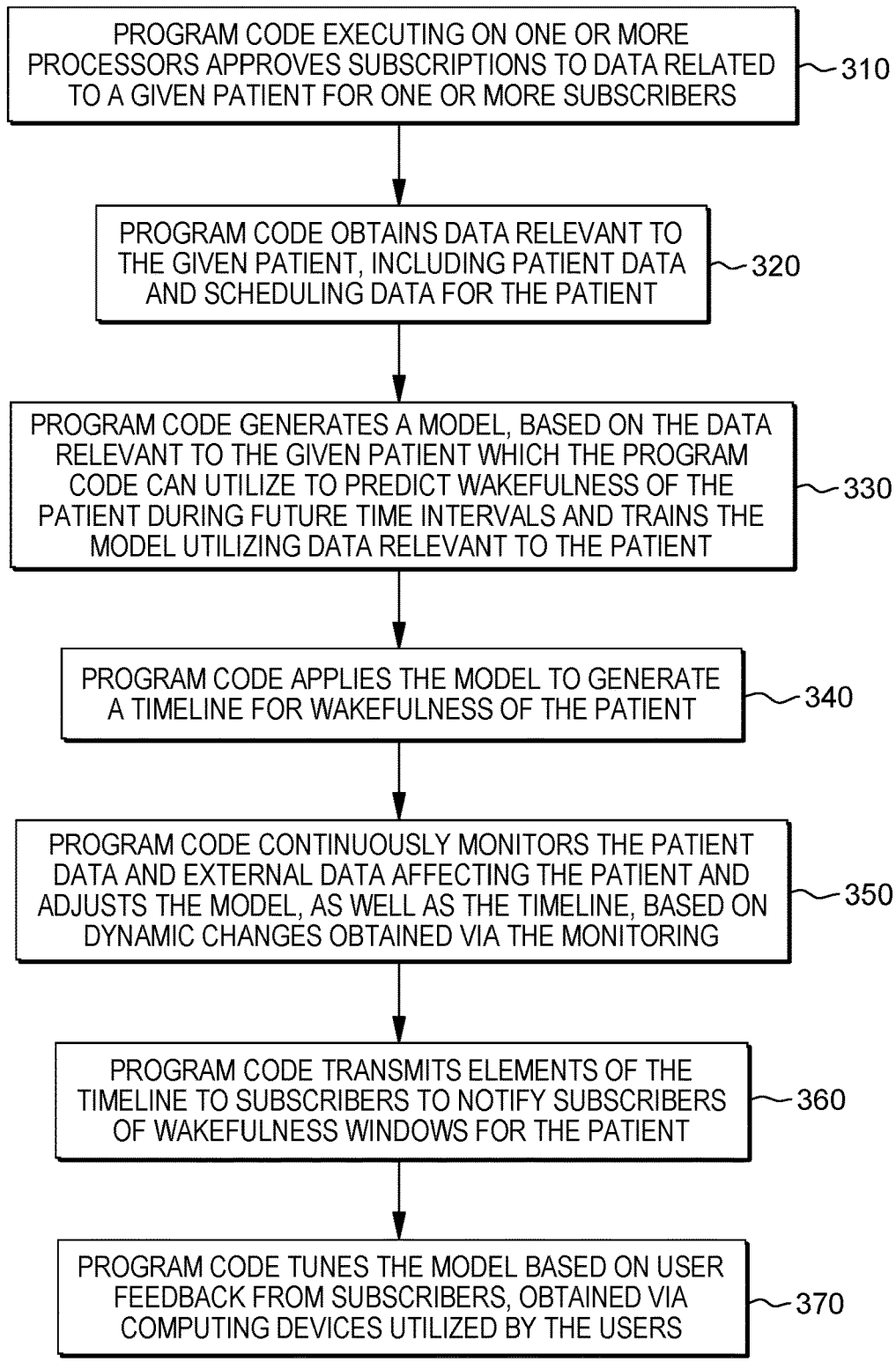
FIG. 3 is a workflow illustrating certain aspects of an embodiment of the present invention.

FIG. 3 is a workflow 300 that illustrates certain aspects of some embodiments of the present invention. A patient initially opts into participating in the notifications of wakefulness generated by program code in embodiments of the present invention and indicates what data sources, controlled by the patient, the program code can access in generating the model, which the program code will utilize to generate the notifications. Once a given patient has subscribed, in some embodiments of the present invention, program code executing on one or more processors approves subscriptions to data related to a given patient for one or more subscribers (310). The subscriber authorization process can include submissions being individually approved by a patient and, optionally, an administrator, and/or automatic approval of subscribers based on the subscribers providing relevant credentials through an interface to a computing node accessible to the one or more processors executing the program code. In the case of automatic approval, the patient, upon subscribing to participate in the notifications, the program code can provide the patient with credentials, which the patient can share with individuals the patients wishes to be subscribed. Both subscription procedures and alerts provided by the program code conform to best privacy and security practices. For example, alerts provided by the program code, to which a user subscribes, in some embodiments of the present invention, do not include any personally identifiable information, but, rather, indicate probabilities that a patient will be awake during a defined time interval. In some embodiments of the present invention, the name of the patient is not included in the alerts. This indication can be provided by the program code in a user-friendly manner through a graphical user interface on a client computing device, such as utilizing colors to indicate likelihood of wakefulness (e.g., red/yellow/green).

Based on privacy preferences indicated by the patient at subscription (or updated at a later time), the program code obtains data relevant to the given patient, including patient data and scheduling data for the patient (320). Data relevant to a patient can include patient data that the program code obtains from a variety of sources, including but not limited to: 1) physical sensor data relevant to wakefulness (e.g., heart rate, muscle tension, oxygen levels, breathing, motion detection); 2) patient condition (e.g., reason for hospitalization/treatment); and 3) treatment information (e.g., from an electronic patient record, including information about medication and interactions that could potentially affect patient alertness). Regarding the last data element, this is relevant to the wakefulness predictions related to a patient because, for example, if a patient is scheduled to have a sedative at a specific time, the program code utilizes the time-frame of the effect of that treatment when generating a model. Data relevant to the patient can also include calendar scheduled events for patient (e.g., appointments for x-rays, CT-scans, or other tests). The program code can utilize these scheduled events as a guide when determining the availability of a patient for guests, however, since these events can be rescheduled, the program code in embodiments of the invention can monitor a patient schedule on an ongoing or intermittent basis such that the model generated by the program code reflects a most current version of the schedule of the patient.

The program code generates a model, based on the (authorized) data relevant to the given patient which the program code can utilize to predict wakefulness of the patient during future time intervals and trains the model utilizing data relevant to the patient (330). As part of generating the model, the program code trains or initializes the model, as discussed in FIGS. 1-2. The program code can initialize the model based on data related to the health condition of the patient, including but not limited to, medication information, treatment information, as related to patients that the program code determines are similar to the patient, as well as, in some embodiments of the present invention, historical data related to the patient. In some embodiments of the present invention, the program code generates various scenarios for wakefulness patterns based on the type of care the patient is receiving (e.g., acute or short term care versus long term care). As depicted in FIG. 2, the program code can utilize additional data from existing patient information (e.g., MIMIC III) as a source of training data to utilize in training the model. By utilizing this existing patient information, with the permission of the patient and any relevant administrative authority, the program code can improve the pattern detection and learning utilized by the program code to generate the prediction model. Existing patient information, including data relevant to certain medications that the given patient is scheduled to receive would assist in prediction of wakefulness timing because the general patient data would indicate, for example, the sedation time windows of the medication doses, which the program code could utilize in an initial model and refine based on monitoring responses from the specific patient. In the case where the patient limits personal information access, the existing patient information, which is publicly accessible, would be particularly helpful to the program code in generating a model.

The program code applies the model to generate a timeline for wakefulness of the patient (340). Upon generating the timeline, the program code continues to monitor the data sources relevant to and authorized by the patient (and any relevant authority) and adjust the model and the timeline, based on the changes to the model, to reflect a most current understanding of intervals in the timeline where there exists a threshold probability that the patient is awake and available for visitors. The timeline reflects windows of predicted wakefulness for the patient. In some embodiments of the present invention, if sensors monitoring vital signs of a patient and environmental factors within a vicinity of a patient indicate a wakeful state, the program code updates the model to predict wakefulness for several granularities of near-future time slices (e.g., next 10 minutes, next 30 minutes, next hour) with decay rates of prediction accuracy. Additionally, the program code can utilize the model to interpolate how the sensor data relates to the current model state.

The program code continuously monitors the patient data and external data affecting the patient and adjusts the model, as well as the timeline, based on dynamic changes obtained via the monitoring (350). In embodiments of the present invention, when the program code obtains data from sensors, in real-time, which conflicts with modeled patterns, the program code can either override the predictions of the model and/or update the model to comport with the anomalies. Based on the one-off change or the model revision, the program code updates the timeline. An example of external data that affects the patient is scheduling data related to the patient. If a patient is scheduled for a given procedure, the timing of the procedure would impact the wakefulness predictions for the given patient. Based on the scheduling changes, the program code can update the model and generate an updated timeline.

As understood by one of skill in the art, the program code through training and iterative processing can establish baseline values that represent wakefulness patterns for a given patient. The program code can cognitively analyze the data to identify these patterns and integrate the patterns into the predictive model. Certain values obtained by the program code can deviate without expected ranges from the baseline, but as the overall health of the patient changes, the baseline value can also change. In embodiments of the present invention where the patient and relevant administrative authorities have authorized access to electronic medical records, the program code can obtain updated health-related data describing the health condition of a patient and update various baselines that comprise the model based on the changes. The program code modifies the generated predictive timelines based on continuously obtaining data, including but not limited to, sensor data, treatment details and/or scheduled events. The program code updates baselines based on threshold changes (changes of a certain degree and/or of a certain quantity), but can also adjust timelines, but not the model, to accommodate one-off changes to the timeline based on data outside of a standard deviation from the model being obtained by the program code in a manner that does not indicate a baseline change. In embodiments of the present invention, based on receiving an outlier event (e.g., via sensor data), the program code can override an existing timeline to populate the timeline with the outlier without changing the model. Based on receiving a threshold number of outliers, the program code can update the model itself.

The program code transmits elements of the timeline to (authorized) subscribers to notify subscribers of wakefulness windows for the patient (360). When the users subscribe, the users may indicate certain alert preference, which the program code can access and conform to, when transmitting alerts. For example, certain users may elect to receive alerts only when their computing devices are within a certain vicinity of the patient. The user may also select a manner in which the user desires to receive the alerts (e.g., email, text, phone, and/or other notification method). Certain subscribers can also receive certain availabilities for given time periods based on access levels. For example, a patient or other administrator may assign subscribers to different designated visitor levels, and based on the levels, the subscribers may or may not be eligible to visit the patient during certain periods. Thus, the program code will only alert a user of a wakeful period that occurs during a time when a visitor of the level of the user is eligible to visit the patient. In some embodiments of the present invention, either a user and/or an administrator has the option of adjusting a sensitivity of the threshold for notification. Thus, while some subscribers will opt to receive alerts when the patient is predicted to be merely conscious, other users can opt to receive alerts when the patient is predicted to be both awake and fully alert.

The program code tunes the model based on user feedback from subscribers, obtained via computing devices utilized by the users (370). Specifically, the program code can combine predictions for defined time windows in the timeline with baseline probabilities that are improved over time due, and revise/correct these values by obtaining feedback from individual users (subscribers). For example, a subscriber can receive a notification that the patient is predicted to be awake at a given time, arrive to visit the patient at the time, and learn that the patient is not awake. The subscriber can provide this data to the program code via a computing interface. Upon receipt of this data, the program code analyzes the discrepancy and revises the model in accordance with this inconsistency. In this manner, the model is continuously improved by the program code and personalized to the patient.

Embodiments of the present invention include a computer-implemented method, a computer program product, and a computer system, where program code executed by one or more processors progressively obtains data related to medical treatment and a current physical state of a given patient from a patient monitoring system, an electronic medical records system, and a scheduling system. The program code cognitively analyzes the data to identify potential patient behavioral patterns of the given patient. The program code obtains general patient data. The program code correlates the general patient data with a portion of the progressively obtained data to identify one or more elements in the general patient data with a potential impact on the identified potential patient behavioral patterns. The program code determines impacts of the one or more elements on the identified potential behavioral patterns and applying the impacts to generate a data structure comprising baseline behavioral patterns, where the data structure comprises a predictive model to utilize in determining one or more probabilities that the given patient will exhibit one or more behaviors comprising the baseline behavioral patterns during a defined future time interval. The program code applies the predictive model, to the defined future time interval, where the applying comprises generating a timeline comprising the future time interval, where the timeline is segmented into one or more sub-intervals, where a probability of the one or more probabilities is assigned to each sub-interval of the one or more sub-intervals. The program code transmits the timeline to authorized users, via computing nodes communicatively coupled to the one or more processors via an Internet connection.

In some embodiments of the present invention, the one or more behaviors comprise wakefulness and alertness.

In some embodiments of the present invention, the patient monitoring system comprises one or more sensors located proximate to the given patient.

In some embodiments of the present invention, the data related to the medical treatment and the current physical state of the given patient from the patient monitoring system is selected from the group consisting of: physiological data, heart rate, blood pressure, blood oxygen saturation, respiration, movement data indicating a restful state, movement data indicating an active state, temperature, ambient light readings, and noise readings.

In some embodiments of the present invention, the data related to the medical treatment and the current physical state of the given patient comprises medication scheduling information, where the general patient data comprises anticipated impacts of various medications on behavioral patterns of patients, and the one or more elements comprise one or more medications comprising the medication scheduling information.

In some embodiments of the present invention, the data related to the medical treatment and the current physical state of the given patient from the scheduling system comprises one or more appointments related to one or more medical procedures scheduled for the given patient, and generating the timeline comprises adjusting a portion of the one or more probabilities, where the portion is assigned to specific sub-intervals of the one or more sub-intervals, based on the one or more appointments being scheduled during the specific sub-intervals.

In some embodiments of the present invention, the program code obtains one or more subscription requests from users for access to the timeline of the given patient. The program code authorizes a portion of the users to receive transmissions, from the one or more processors, of the timeline; the portion comprises the authorized users.

In some embodiments of the present invention, the program code obtains additional data related to the medical treatment and the current physical state of the given patient from the patient monitoring system, the electronic medical records system, and the scheduling system. The program code cognitively analyzes the additional data, by applying the predictive model to determine is the additional data is consistent with the baseline behavioral patterns. Based on determining that the additional data is inconsistent with the baseline behavioral patterns, the program code updates the timeline.

In some embodiments of the present invention, the program code transmits the updated timeline to the authorized users.

In some embodiments of the present invention, the program code updates the model, based on the additional data.

In some embodiments of the present invention, the program code obtains, via one or more of the computing nodes, after passage of a given sub-interval, feedback regarding veracity of one or more probabilities assigned to the given sub-interval. The program code updates the predictive model based on the feedback.

Referring now to FIG. 4, a schematic of an example of a computing node, which can be a cloud computing node 10. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove. In an embodiment of the present invention the computing resources executing the program code referenced in FIGS. 1-3 can each be understood as a cloud computing node 10 (FIG. 4) and if not a cloud computing node 10, then one or more general computing nodes that include aspects of the cloud computing node 10. Various examples of these resources may, together, comprise a hybrid cloud.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 that can be utilized as cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs). Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter). Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
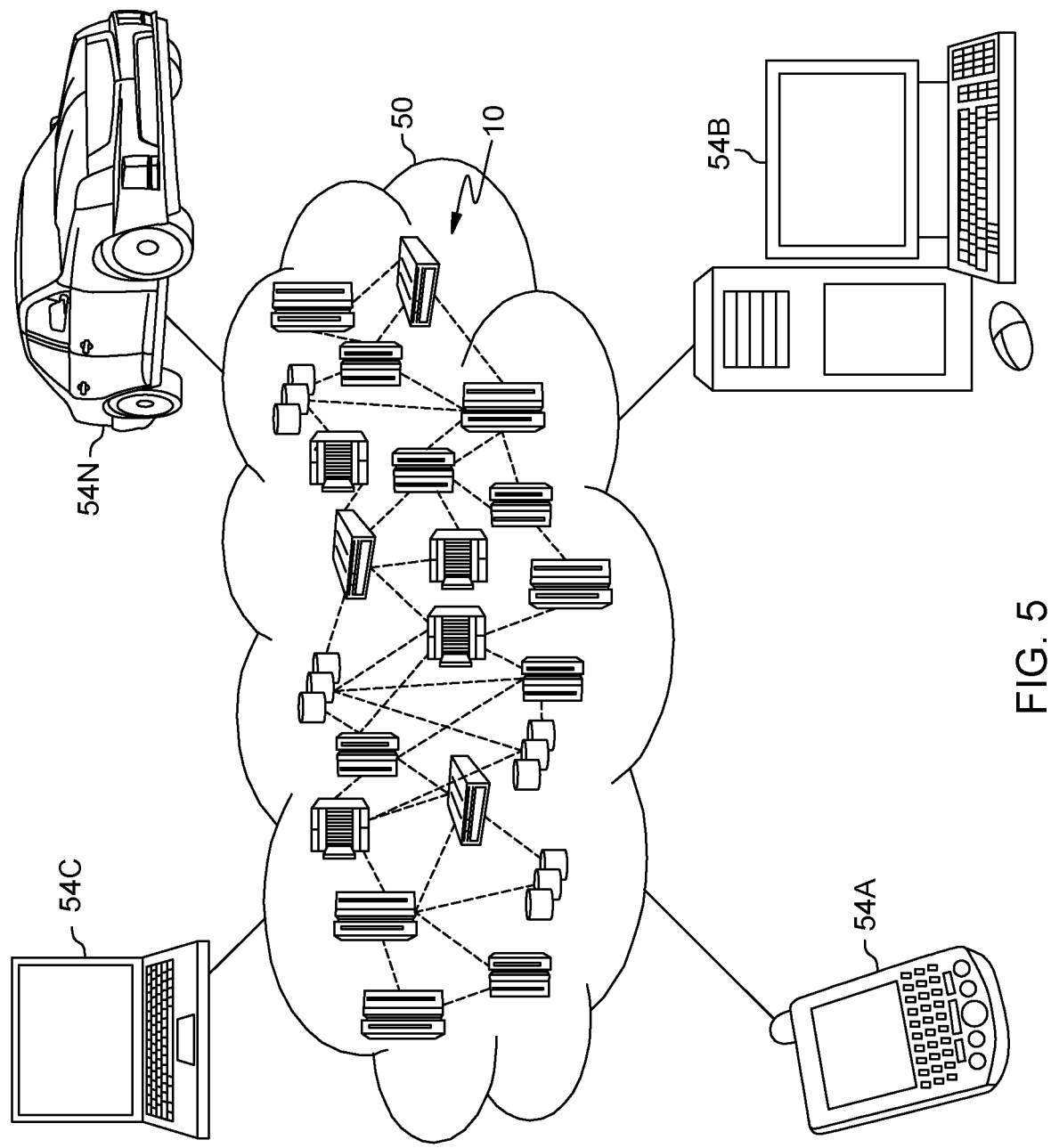
FIG. 5 depicts a cloud computing environment according to an embodiment of the present invention.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
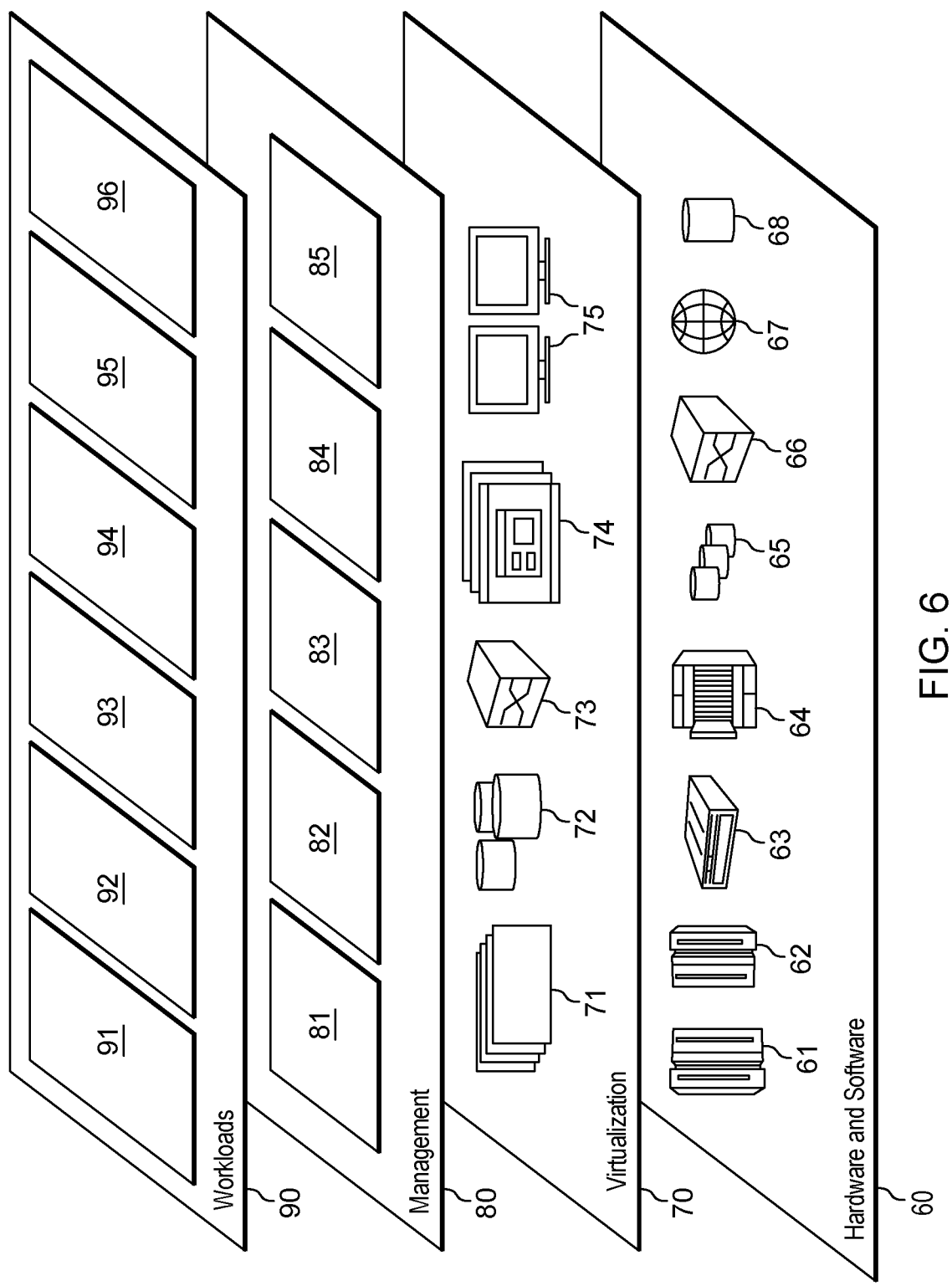
FIG. 6 depicts abstraction model layers according to an embodiment of the present invention.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and generation of a predictive model 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A computer-implemented method, comprising:
    progressively obtaining, by one or more processors, data related to medical treatment and a current physical state of a given patient from a patient monitoring system, an electronic medical records system, and a scheduling system, wherein the patient monitoring system comprises Internet of Things devices and radio-frequency identification tags, wherein the Internet of Things devices and the radio-frequency identification tags are located proximate to the given patient and monitor wakefulness and alertness of the given patient;
    cognitively analyzing, by the one or more processors, the data to identify potential patient behavioral patterns of the given patient;
    obtaining, by the one or more processors, general patient data;
    correlating, by the one or more processors, the general patient data with a portion of the progressively obtained data to identify one or more elements in the general patient data with a potential impact on the identified potential patient behavioral patterns;
    determining, by the one or more processors, impacts of the one or more elements on the identified potential behavioral patterns and applying the impacts to generate a data structure comprising baseline behavioral patterns, wherein the data structure comprises a predictive model to utilize in determining one or more probabilities that the given patient will exhibit one or more behaviors comprising the baseline behavioral patterns during a defined future time interval;
    applying, by the one or more processors, the predictive model, to the defined future time interval, wherein the applying comprises generating a timeline comprising the future time interval, wherein the timeline is segmented into one or more sub-intervals, wherein a probability of the one or more probabilities is assigned to each sub-interval of the one or more sub-intervals, wherein the probabilities comprise likelihoods of wakefulness and availability for the given patient in each sub-interval of the one or more sub-intervals in a predicted location;
    transmitting, by the one or more processors, the timeline to authorized users, via computing nodes communicatively coupled to the one or more processors via an Internet connection;
    obtaining, by the one or more processors, via one or more of the computing nodes, after passage of a given sub-interval, feedback regarding veracity of one or more probabilities assigned to the given sub-interval, wherein the feedback comprises passive feedback;
    continuously obtaining, by the one or more processors, during the given sub-interval, data from the Internet of Things devices indicating the wakefulness and the alertness of the given patient during the sub-interval; and
    continuously updating, by the one or more processors, the predictive model based on the data and the feedback.

2. The computer-implemented method of claim 1, wherein the one or more behaviors comprise wakefulness and alertness, and wherein the patient monitoring system comprises one or more sensors located proximate to the given patient, wherein the one or more sensors provide the passive feedback.

3. The computer-implemented method of claim 1, wherein the data related to the medical treatment and the current physical state of the given patient from the patient monitoring system is selected from the group consisting of: physiological data, heart rate, blood pressure, blood oxygen saturation, respiration, movement data indicating a restful state, movement data indicating an active state, temperature, ambient light readings, and noise readings.

4. The computer-implemented method of claim 1, wherein the data related to the medical treatment and the current physical state of the given patient comprises medication scheduling information, wherein the general patient data comprises anticipated impacts of various medications on behavioral patterns of patients, and wherein the one or more elements comprise one or more medications comprising the medication scheduling information.

5. The computer-implemented method of claim 1, wherein the data related to the medical treatment and the current physical state of the given patient from the scheduling system comprises one or more appointments related to one or more medical procedures scheduled for the given patient, and wherein generating the timeline comprises adjusting a portion of the one or more probabilities, wherein the portion is assigned to specific sub-intervals of the one or more sub-intervals, based on the one or more appointments being scheduled during the specific sub-intervals.

6. The computer-implemented method of claim 1, further comprising:
    obtaining, by the one or more processors, one or more subscription requests from users for access to the timeline of the given patient; and
    authorizing, by the one or more processors, a portion of the users to receive transmissions, from the one or more processors, of the timeline, wherein the portion comprises the authorized users.

7. The computer-implemented method of claim 1, further comprising:
    obtaining, by one or more processors, additional data related to the medical treatment and the current physical state of the given patient from the patient monitoring system, the electronic medical records system, and the scheduling system;
    cognitively analyzing, by the one or more processors, the additional data, by applying the predictive model to determine is the additional data is consistent with the baseline behavioral patterns;
    based on determining that the additional data is inconsistent with the baseline behavioral patterns, updating, by the one or more processors, the timeline; and
    updating, by the one or more processors, the model, based on the additional data.

8. The computer-implemented method of claim 7, further comprising:
    transmitting, by the one or more processors, the updated timeline to the authorized users.

9. The computer-implemented method of claim 1, wherein the feedback further comprises active user feedback.

10. The computer-method of claim 1, wherein the probability of the one or more probabilities assigned to each sub-interval of the one or more sub-intervals is a forecast of likely times of wakefulness and availability for the given patient.

11. The computer-implemented method of claim 1, further comprising:
creating, by the one or more processors, the authorized user, the creating comprising:
obtaining, by the one or more processors, requests from users to obtain the timeline;
automatically providing, by the one or more processors, a listing of the requests to the given patient via an interface;
obtaining, by the one or more processors, for each request of the requests, via the interface, from the given patient, an approval or a denial of the request; and
designating, by the one or more processors, each approved user an authorized user.

12. A computer program product comprising:
a computer readable storage medium readable by one or more processors and storing instructions for execution by the one or more processors for performing a method comprising:
progressively obtaining, by the one or more processors, data related to medical treatment and a current physical state of a given patient from a patient monitoring system, an electronic medical records system, and a scheduling system, wherein the patient monitoring system comprises Internet of Things devices and radio-frequency identification tags, wherein the Internet of Things devices and the radio-frequency identification tags are located proximate to the given patient and monitor wakefulness and alertness of the given patient;
cognitively analyzing, by the one or more processors, the data to identify potential patient behavioral patterns of the given patient;
obtaining, by the one or more processors, general patient data;
correlating, by the one or more processors, the general patient data with a portion of the progressively obtained data to identify one or more elements in the general patient data with a potential impact on the identified potential patient behavioral patterns;
determining, by the one or more processors, impacts of the one or more elements on the identified potential behavioral patterns and applying the impacts to generate a data structure comprising baseline behavioral patterns, wherein the data structure comprises a predictive model to utilize in determining one or more probabilities that the given patient will exhibit one or more behaviors comprising the baseline behavioral patterns during a defined future time interval;
applying, by the one or more processors, the predictive model, to the defined future time interval, wherein the applying comprises generating a timeline comprising the future time interval, wherein the timeline is segmented into one or more sub-intervals, wherein a probability of the one or more probabilities is assigned to each sub-interval of the one or more sub-intervals, wherein the probabilities comprise likelihoods of wakefulness and availability for the given patient in each sub-interval of the one or more sub-intervals in a predicted location;
transmitting, by the one or more processors, the timeline to authorized users, via computing nodes communicatively coupled to the one or more processors via an Internet connection;
obtaining, by the one or more processors, via one or more of the computing nodes, after passage of a given sub-interval, feedback regarding veracity of one or more probabilities assigned to the given sub-interval, wherein the feedback comprises passive feedback;
continuously obtaining, by the one or more processors, during the given sub-interval, data from the Internet of Things devices indicating the wakefulness and the alertness of the given patient during the sub-interval; and
continuously updating, by the one or more processors, the predictive model based on the data and the feedback.

13. The computer program product of claim 12, wherein the one or more behaviors comprise wakefulness and alertness.

14. The computer program product of claim 12, wherein the patient monitoring system comprises one or more sensors located proximate to the given patient.

15. The computer program product of claim 12, wherein the data related to the medical treatment and the current physical state of the given patient from the patient monitoring system is selected from the group consisting of: physiological data, heart rate, blood pressure, blood oxygen saturation, respiration, movement data indicating a restful state, movement data indicating an active state, temperature, ambient light readings, and noise readings.

16. The computer program product of claim 12, wherein the data related to the medical treatment and the current physical state of the given patient comprises medication scheduling information, wherein the general patient data comprises anticipated impacts of various medications on behavioral patterns of patients, and wherein the one or more elements comprise one or more medications comprising the medication scheduling information.

17. The computer program product of claim 12, wherein the data related to the medical treatment and the current physical state of the given patient from the scheduling system comprises one or more appointments related to one or more medical procedures scheduled for the given patient, and wherein generating the timeline comprises adjusting a portion of the one or more probabilities, wherein the portion is assigned to specific sub-intervals of the one or more sub-intervals, based on the one or more appointments being scheduled during the specific sub-intervals.

18. The computer program product of claim 12, the method further comprising:
obtaining, by the one or more processors, one or more subscription requests from users for access to the timeline of the given patient; and
authorizing, by the one or more processors, a portion of the users to receive transmissions, from the one or more processors, of the timeline, wherein the portion comprises the authorized users.

19. The computer program product of claim 12, the method further comprising:
obtaining, by one or more processors, additional data related to the medical treatment and the current physical state of the given patient from the patient monitoring system, the electronic medical records system, and the scheduling system;

cognitively analyzing, by the one or more processors, the additional data, by applying the predictive model to determine is the additional data is consistent with the baseline behavioral patterns; and based on determining that the additional data is inconsistent with the baseline behavioral patterns, updating, by the one or more processors, the timeline.

20. A system comprising:

a memory;

one or more processors in communication with the memory;

program instructions executable by the one or more processors via the memory to perform a method, the method comprising:

progressively obtaining, by the one or more processors, data related to medical treatment and a current physical state of a given patient from a patient monitoring system, an electronic medical records system, and a scheduling system, wherein the patient monitoring system comprises Internet of Things devices and radio-frequency identification tags, wherein the Internet of Things devices and the radio-frequency identification tags are located proximate to the given patient and monitor wakefulness and alertness of the given patient;

cognitively analyzing, by the one or more processors, the data to identify potential patient behavioral patterns of the given patient;

obtaining, by the one or more processors, general patient data;

correlating, by the one or more processors, the general patient data with a portion of the progressively obtained data to identify one or more elements in the general patient data with a potential impact on the identified potential patient behavioral patterns;

determining, by the one or more processors, impacts of the one or more elements on the identified potential behavioral patterns and applying the impacts to generate a data structure comprising baseline behavioral patterns, wherein the data structure comprises a predictive model to utilize in determining one or more probabilities that the given patient will exhibit one or more behaviors comprising the baseline behavioral patterns during a defined future time interval;

applying, by the one or more processors, the predictive model, to the defined future time interval, wherein the applying comprises generating a timeline comprising the future time interval, wherein the timeline is segmented into one or more sub-intervals, wherein a probability of the one or more probabilities is assigned to each sub-interval of the one or more sub-intervals, wherein the probabilities comprise likelihoods of wakefulness and availability for the given patient in each sub-interval of the one or more sub-intervals in a predicted location;

transmitting, by the one or more processors, the timeline to authorized users, via computing nodes communicatively coupled to the one or more processors via an Internet connection;

obtaining, by the one or more processors, via one or more of the computing nodes, after passage of a given sub-interval, feedback regarding veracity of one or more probabilities assigned to the given sub-interval, wherein the feedback comprises passive feedback;

continuously obtaining, by the one or more processors, during the given sub-interval, data from the Internet of Things devices indicating the wakefulness and the alertness of the given patient during the sub-interval; and continuously updating, by the one or more processors, the predictive model based on the data and the feedback.

* * * * *